United States Patent [19]

Aki et al.

[11] Patent Number: 4,976,706

[45] Date of Patent: * Dec. 11, 1990

[54] SHEET MATERIAL OF GERMANIUM AND CERAMIC FOR SKIN CONTACT MEDICAL TREATMENT

[75] Inventors: Osami Aki, Kawanishi; Yoshinori Yamamoto, Urayasu; Masayoshi Matsuoka, Habikino; Hideki Tachibana, Izumiotsu; Setsumi Tanase, Sen-nangun, all of Japan

[73] Assignees: Tachibana Textile Fabrics, Co., Ltd.; Takeda Chemical Industries, Ltd., both of Osaka, Japan

[ * ] Notice: The portion of the term of this patent subsequent to Dec. 12, 2007 has been disclaimed.

[21] Appl. No.: 366,135

[22] Filed: Jun. 14, 1989

[30] Foreign Application Priority Data

Jun. 15, 1988 [JP] Japan .................................. 63-149053

[51] Int. Cl.$^5$ .............................................. A61F 13/00
[52] U.S. Cl. ..................................... 604/304; 604/20; 128/399
[58] Field of Search .................... 604/20, 23, 289, 290, 604/291, 307, 304; 128/399, 401, 155, 156; 357/28, 81

[56] References Cited

U.S. PATENT DOCUMENTS 4,781,705 11/1988 Shephard et al. ................... 604/304

OTHER PUBLICATIONS

Derwent Accession No. 87-309163.
Derwent Accession No. 87-303614.
Derwent Accession No. 88-087891.
Derwent Accession No. 87-133273.

*Primary Examiner*—Alan W. Cannon
*Attorney, Agent, or Firm*—Wenderoth, Lind & Ponack

[57] ABSTRACT

A sheet material for skin contact medical treatment at least one part of which is a therapeutically effective part comprising germanium and ceramic which irradiates far infrared rays by heating, said germanium and ceramic being provided within a distance of 0 to 3 cm in said therapeutically effective part. A composition of therapeutically effective materials for skin contact medical treatment which comprises germanium powder and ceramic powder which irradiates far infrared rays by heating is also disclosed.

9 Claims, 2 Drawing Sheets

SHEET MATERIAL OF GERMANIUM AND CERAMIC FOR SKIN CONTACT MEDICAL TREATMENT

FIELD OF THE INVENTION

The present invention relates to a sheet material for skin contact medical treatment. More particularly, it relates to a sheet material for medical treatment which has therapeutically effective parts comprising germanium and a far infrared ray irradiating ceramic and is used by bringing it into contact with the skin such as a diseased part of the human body, an affected spot of the skin and the like.

BACKGROUND OF THE INVENTION

As can be seen from the fact that well known herb medicines such as ginseng, a bracket fungus of the genus Fomes and, the like contain organic germanium, recently, the use of germanium has been noted in medical treatment.

Usually, organic germanium is administered orally. On the other hand, inorganic germanium is locally applied to the skin in the form of a magnetic material for medical treatment by bringing it into contact with an affected spot of the skin and the like. Although these germanium materials manifest analgetic and antiphlogistic effects such as therapeutic effect on stiff shoulders, lumbago and muscular ache, its mechanism has not yet been clarified.

However, there is an opinion that, when germanium is applied to a diseased part, it removes an abnormal electric potential of the human body by electron interchange to bring the body back to the normal electric potential because:

(1) germanium is apt to be positively charged due to escape of the peripheral electron (i.e., germanium has a strong electrophilic properties); and (2) a diseased part or a body part with stiffness or pain generally has an increased electron potential.

As the conventional technique for bringing the above inorganic germanium into contact with the skin, Japanese Patent Laid Open Publication No. 117187/1979 discloses germanium which is a metallic mass in the form of a substantially circular small disk and is brought into contact with the skin by pressing it against the skin with a plaster or the like. In this material for medical treatment, germanium is formed in a mass to concentrate its stimulation on an affected spot of the skin.

However, when the material is applied to the skin over a long period of time, a depressed mark is left on the skin, or a pain is felt by pressing it against the skin. Further, since a contact area of the skin is diminished in order to concentrate stimulation, it is difficult for laymen to apply the material to an affected spot, exactly and satisfactorily. Furthermore, in the above conventional technique, the fundamental effect on the human body is limited to the electrical activity of germanium alone and, therefore, its therapeutic effect is naturally limited.

On the other hand, some ceramics irradiate far infrared rays by absorption of heat energy, when they are heated, and it has been known that, when the human body is exposed to such far infrared rays, they manifest various effects such as rise in deep subcutaneous temperature, angiotelectasia, enhancement of blook circulation and metabolism, mitigation of sensory nerves, regulation of autonomic nerves and the like.

The present inventors have sought such a far infrared ray irradiating ceramic, and have found that, when the ceramic is used together with germanium, effective skin contact medical treatment can be achieved due to synergism of activities of germanium and the ceramic and, when a material for skin contact medical treatment is in the form of a sheet, various advantages can be otained.

Japanese Patent Laid Open Publication No. 180979/1987 discloses a heating element of a warmer for warming the human body to enhance metabolism thereof which is a sintered molded article of a mixture of a far infrared ray irradiating ceramic, an oxide of a specific metal such as iron, manganese, chromium or the like, and metallic germanium or germanium oxide. However, this heating element is used by heating with a nichrome wire heater or the like and is completely different from a sheet material for skin contact medical treatment.

OBJECTS OF THE INVENTION

One object of the present invention is to provide a sheet material for skin contact medical treatment which is comfortable and can be readily and properly applied to an affected spot of the skin, and which is superior to the conventional medical treatment by germanium.

Another object of the present invention is to provide a composition of therapeutically effective materials useful for the production of the sheet material of the present invention.

These objects as well as other objects and advantages of the present invention will become apparent to those skilled in the art from the following description with reference to the accompanying drawings.

SUMMARY OF THE INVENTION

Figure 1:
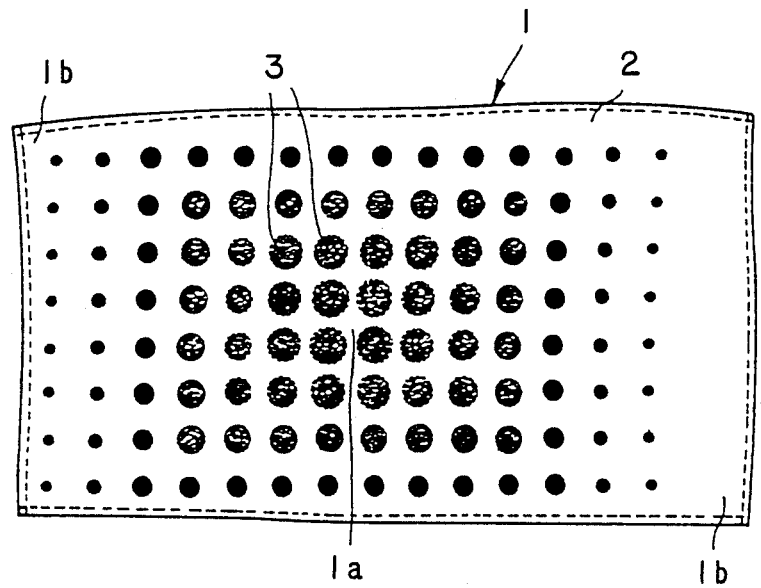
FIG. 1 is a schematic plan view illustrating one embodiment of the sheet material for skin contact medical treatment of the present invention.

According to the present invention, there is provided a sheet material for skin contact medical treatment at least one part of which is a therapeutically effective part comprising germanium and ceramic which irradiates far infrared rays by heating, said germanium and ceramics being provided within a distance of 0 to 3 cm of each other in said therapeutically effective part. As one preferred embodiment of the sheet material of the present invention, there is provided a cloth coated with a composition of therapeutically effective materials comprising germanium power and ceramic powder which irradiates far infrared rays by heating.

The sheet material of the present invention can be readily applied to the skin and can smoothly fit the human body. Further, although the mechanism is unclear, it is considered that the therapeutic effect of germanium is enhanced by action of heat rays of far infrared rays irradiated from the ceramic by heating with the body temperature.

The present invention also provides a composition for skin contact medical treatment which comprises germanium powder and ceramic powder which irradiates far infrared rays by heating.

DETAILED DESCRIPTION OF THE INVENTION

Germanium to be used in the present invention may be any germanium or germanium containing substance including inorganic germanium, an organic germanium complex containing 2 to 10 carbon atoms and the like. In the case of inorganic germanium, preferably, it has a purity of not less than 99.9%.

The composition of the ceramic to be used in the present invention is not limited to a specific one insofar as it irradiates far infrared rays by heating with the body temperature. Examples thereof include far infrared ray irradiating ceramics obtained by sintering finely divided powder or previously calcined finely divided powder composed of $ZrO_2$, $MgO$, $Al_2O_3$, $SiO_2Cr_2O_3$, $TiO_2$, $Fe_2O_3$ and the like alone or mixtures thereof, or by pulverizing these substances without sintering. Preferably, the wavelength of far infrared rays irradiated is about 3 to 16 $\mu$, particularly, about 5 to 16 $\mu$ because of its strong thermal resonance effect. However, insofar as thermal effect is obtained to a certain extent, the wavelength is not limited thereto.

The sheet material for skin contact medical treatment of the present invention has at least one therapeutically effective part comprising germanium and the ceramic provided within a distance of 0 to 3 cm of each other therein. When the distance between germanium and the ceramic exceeds 3 cm, synergistic effect on therapeutic activity of germanium by the ceramic as described above is hardly expected. Preferably, the distance between germanium and the ceramic is 0 cm. That is, they are brought into contact with each other, or uniformly mixed in the form of powder.

The configuration of the sheet is not limited to a specific one and the sheet itself may be woven or knitted fabrics, unwoven fabrics, various synthetic resin films, preferably those having gas permeability, and the like.

The therapeutically effective part can be provided continuously or discontinuously on the sheet and the weight ratio of germanium (as inorganic pure germanium; hereinafter the amount of germanium is according to the same manner unless otherwise stated): the ceramic in the therapeutically effective part is preferably 3 to 40 : 97 to 60. The sheet can have a single therapeutically effective part or plural therapeutically effective parts.

For example, the therapeutically effective part can be provided by weaving or knitting yarns containing germanium and the ceramic in the above ratio into a woven or knitted fabric or an unwoven fabric. Examples of such yarns include those obtained by applying a coating which is prepared by dispersing a powder mixture of finely divided metallic powder of germanium and a finely divided sintered ceramic powder in a suitable solvent and admixing the resulting dispersion with an adhesive such as acrylic resin, polyurethane resin, polyester resin, silicone resin or the like on suitable conventional yarns and removing the solvent according to a known technique. Such yarns can also be obtained by coating suitable conventional yarns with germanium and ceramic according to known chemical desposition or physical deposition techniques.

In the present invention, the entire sheet material can be composed of these yarns, or a part of the sheet material can be composed of these yarns and the remaining part can be composed of conventional yarns.

Alternatively, the sheet material of the present invention can be prepared by laminating a germanium thin film and a ceramic thin film. The germanium thin film and the ceramic thin film can be obtained according to a known method. In such a laminate, when the inner layer is composed of the ceramic film and the outer layer (i.e., the layer to be brought into contact with the skin) is composed of the germanium film, it is possible to coat the entire surface of the ceramic film with the germanium film because the body temperature is transmitted to the ceramic film through the germanium film and far infrared rays irradiated from the ceramic film can permeate through the germanium film to reach the human body. On the other hand, when the inner layer is composed of the germanium film and the outer layer is composed of the ceramic layer, the ceramic film should be coated discontinuously so that the germanium layer is partly exposed to the human body so that the electrical activity of the germanium layer reaches the human body.

Further, the sheet material of the present invention can be prepared by coating at least a part of a base sheet such as a woven or knitted fabric, an unwoven fabric, resin coated cloth, leather cloth, a synthetic resin film or the like with a coating material comprising germanium and the ceramic which irradiates far infrared rays by heating according to a known method to obtain the therapeutically effective part.

The coating can be carried out by printing a powder mixture of germanium powder and ceramic powder with an adhesive such as polyvinyl alcohol, acrylic resin, polyurethane resin, polyester resin, silicone resin or the like on a part of or the entire surface of the base sheet, or by applying a coating such as that disclosed above on the surface of the base sheet. Further, the above powder mixture can be coated on the base sheet by deposition, sputtering or the like.

In addition, the above laminate of germanium film and the ceramic film can be further laminated on the base sheet.

In one preferred embodiment of the present invention, the therapeutic effect of the sheet material can be further enhanced by covering one surface of the therapeutically effective part with a metallic film and bringing the other surface thereof, wherein the therapeutically effective part is exposed, into contact with the skin. Thereby, diffusion of the electrical and heat ray effects can be prevented and the effects can be concentrated on the skin with which the sheet is brought into contact.

For example, the metallic film can be formed by depositing a thin metal film on one surface of the therapeutically effective part, or by adhering a metallic foil thereto. The metal is preferably aluminum from the viewpoint of economy and the like. However, there can be used tin, nickel and the like and the composition thereof is not specifically limited.

In another aspect, the present invention provides a composition of therapeutically effective materials for skin contact medical treatment including the above coating which comprises germanium powder and ceramic powder which irradiates far infrared rays by heating.

The germanium and the ceramic to be used in the composition are those described above an, preferably, they have an average particle size of about 0.1 to 5 μ. The weight ratio of germanium : ceramic in the composition is preferably 3 to 40 : 97 to 60. The total amount of germanium and ceramic in the composition is preferably 15 to 50% by weight.

The composition of the present invention can be prepared according to a known process for producing a conventional coating composition. If necessary, germanium powder and ceramic powder can be dispersed in a solvent such as butyl acetate or the like and, if necessary, admized with an adhesive or film forming resin such as acrylic resin, polyurethane resin, polyester resin, silicone resin or the like to obtain a coating having a solid content of about 5 to 20% by weight. Optionally, the composition can appropriately contain other additives such as blowing agents, surfactants, fillers, colorants and the like.

When the sheet material of the present invention is applied to a diseased part of the human body or an affected spot of the skin as it is or in the form of supporters, underwear and the like prepared therefrom, the therapeutically effective part can be brought into contact with the skin softly without leaving a depressed mark or causing pain due to pressing. Further, in the case that the therapeutically effective part has a relatively larger contact area, it can be brought into contact with an affected spot exactly and satisfactorily only by covering such a spot with the sheet material.

Then, upon applying the sheet material to the skin, the therapeutically effective part is warmed by the body temperature and far infrared rays are irradiated from the ceramic. At the same time, the electrical effect of germanium reaches the skin at the contact part. Thus, both therapeutic effects of germanium and ceramic can be manifested at the same time.

Further, electrophilic properties of germanium are enhanced because germanium absorbs a part of heat energy of far infrared rays irradiated from the ceramic to lose an electron, which increases the positive charged tendency of germanium. Therefore, it is expected that the therapeutic effect of the contact part of the skin is increased.

In addition, as described above, when one surface of the therapeutic effective part is covered with a metallic film such as aluminum film and the other surface is brought into contact with skin, diffusion of the electrical and thermal effects of the sheet toward directions other than the contact part can be prevented and the therapeutic effect can be concentrated on the skin with which the sheet is brought into contact.

Thus, the following advantages can be obtained by the sheet material for skin contact medical treatment of the present invention.

(1) Enhancement of analgetic and antiphlogistic effects of germanium is expected due to thermal effect of far infrared rays irradiated from the ceramic, since in comparision with the therapeutic effect of a conventional material for medical treatment containing germanium alone, heat ray effect of the ceramic is added and the effect of germanium itself is increased. Therefore, the scope of treatment can be expanded and the therapeutic effect can be improved.

(2) In the sheet material of the present invention, the therapeutically effective part in the form of a sheet is softly brought into contact with the body. Therefore, even if the material is used over a long period of time, no depressed mark is left and no pain is felt by pressing the sheet material against the skin.

In addition, the therapeutically effective part can be readily and exactly brought into contact with an affected spot by merely applying the sheet material having a large surface area to the skin to improve the therapeutic effect.

(3) In the case of covering one surface of the therapeutically effective part with a metallic film, the electrical and thermal effects can be concentrated on the body. Thereby, medical treatment can be carried out more effectively.

Hereinafter, the sheet material for skin contact medical treatment of the present invention is further illustrated in detail with reference to the accompanying drawings.

Figure 2:
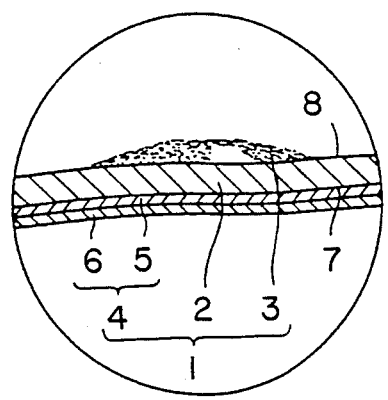
FIG. 2 is a schematic enlarged longitudinal cross section of the material of FIG. 1.

FIG. 1 is a schematic plan view illustrating one embodiment of the sheet material for skin contact medical treatment of the present invention in the form of a cloth and FIG. 2 is a schematic longitudinal cross section of the cloth of FIG. 1.

As shown in FIGS. 1 and 2, the cloth 1 is composed of a commercially available raised pile fabric 2 and plural therapeutically effective parts 3 in the form of circular films which are printed on the fabric 2. The pile fabric 2 is backed with an aluminum foil 4.

In order to produce this sheet material, firstly, a composition for the therapeutically effective part was prepared from germanium powder and sintered ceramic powder irradiating far infrared rays.

The sintered ceramic powder was prepared as follows.

Small amounts of CaO, MgO, and $Y_2O_3$ were added to a powder mixture of $ZrO_2$, $TiO_2$ and $MnO_2$ and the resulting mixture was calcined at 1000° C to obtain stable $ZrO_2$ powder. To this powder was added an organic binder such as phenol resin and the mixture was molded and sintered by heating in a furnace or by high frequency heating to obtain a mass. The mass was pulverized into finely divided powder having an average particle size of 0.1 to 5 μ.

As the main components of the ceramic, the following substances can also be used.
(1) a powder mixture of $ZrO_2$, $SiO_2$ and $Al_2O_3$
(2) a powder mixture of $ZrO_2$, $TiO_2$ and $Al_2O_3$
(3) a powder mixture of $ZrO_2$, MgO and $Fe_2O_3$
(4) a powder mixture of $ZrO_2$, $SiO_2$, $Al_2O_3$ and $Fe_2O_3$
(5) a powder mixture of $SiO_2$, $Al_2O_3$ and $Fe_2O_3$ (in this case, no sintering is required)

Germanium powder was prepared by pulverizing metallic germanium having high purity to obtain finely divided powder having an average particle size of 0.1 to 5μ.

The above finely divided germanium powder and finely divided ceramic powder were mixed in a weight ratio of 10 (germanium): 90 (ceramic) and to the mixture (100 parts by weight) were added an emulsifier (14 parts by weight) such as acrylic ester copolymer, a blowing agent (53 parts by weight) (e.g., acrylic compound, urethane compound, sodium bicarbonate, azide compound, etc.) and an adhesive (3 parts by weight) (e.g., acrylic resin, polyurethane resin, polyester resin such as vinyl, acetate etc., silicone resin, polyvinyl alcohol, etc.). The resulting mixture was kneaded uniformly to obtain the desired composition.

Next, an unwoven fabric 6 on which aluminum thin film 5 was deposited was sewed on the entire back surface 7 of the fabric 2. The therapeutically effective parts 3 in the form of circular films were printed on the surface 8 of the fabric 2 lengthwise and crosswide in checkerboard pattern by using the above composition. Then, the cloth 1 was subjected to heat treatment (for example, at 100° to 130° C. for about 30 seconds to 2 minutes in the case of using acrylic blowing agent or more than 60° C. in the case of using sodium bicarbonate) to expand the therapeutically effective parts and the surfaces of the circular films 3 were formed in convex curved form (see FIG. 2).

As the result, it is possible to provide a suitable pressure to the human body by the cloth 1 without any pain.

Further, in this embodiment, the diameter of each circular film 3 becomes smaller gradually from the center part 1a of the cloth 1 toward the peripheral part 1b. Thereby, when the cloth 1 is applied to the skin, the therapeutically effective parts 3 are concentrated at the center of the contact part.

Alternatively, the therapeutically effective parts 3 can be provided by applying an adhesive to the entire surface of the cloth 1 and then bonding a powder mixture of germanium powder and sintered ceramic powder thereto.

Figure 3:
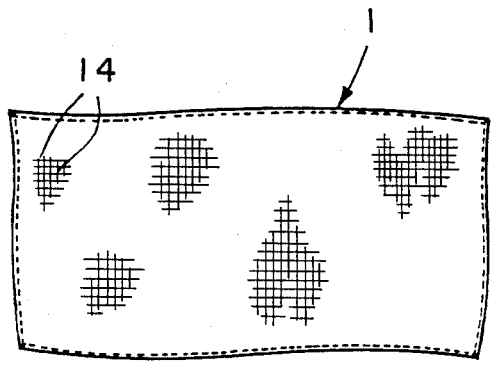
FIG. 3 is a schematic plan view illustrating another embodiment of the sheet material for skin contact medical treatment of the present invention.
Figure 4:
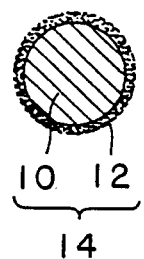
FIG. 4 is a schematic enlarged cross section of yarn which constitutes the material of FIG. 3.

FIG. 3 is a schematic plan view illustrating another embodiment of the sheet material for skin contact medical treatment of the present invention in the form of a cloth and FIG. 4 is a schematic enlarged cross section of yarn which constitutes the cloth of FIG. 3.

In this embodiment, the above-prepared finely divided germanium powder (15 parts by weight) and finely divided sintered far infrared ray irradiating ceramic powder (20 parts by weight) were dispersed in a solvent (62 parts by weight) (e.g., butyl acetate, etc.) by using a dispersing agent (3 parts by weight) (e.g., a polymeric nonionic surfactant, etc.) to obtain a dispersion. A yarn 10 was dipped into this dispersion, or the dispersion was applied on the outer periphery of the yarn 10 and then the yarn was air-dried to obtain the yarn 14 coated with the therapeutically effective materials 12.

A fabric was woven by using the coated yarn 14 and aluminum foil was sewed on the entire back surface of this fabric to obtain the cloth 1 for medical treatment.

In comparison with the sheet material of FIG. 1 wherein the composition of the therapeutically effective materials are printed on the commercially available fabric, the cloth of FIG. 3 has improved resistance to washing and, therefore, it is more suitable for using a longer period of time.

For practically using the cloth shown in FIG. 1 or 3, it can be applied to a diseased part of the human body or an affected spot on the skin with fixing means such as a plaster, a bandage, a supporter or the like.

On the other hand, when the therapeutically effective part layer is coated on one surface of a leather cloth or a resin cloth and adhesion is provided to such a layer, it can be applied to the body without any fixing means. Further, when a bandage, a supporter, an underwear or the like is prepared by using the cloth, no fixing means are required.

The following examples further illustrate the composition of the present invention.

| Ingredient | % by weight |
| --- | --- |
| Acrylic resin foaming binder | 57 |
| Acrylic resin stretch binder | 15 |

-continued

| Ingredient | % by weight |
| --- | --- |
| Urethane cross linking agent | 3 |
| Far infrared irradiating ceramic | 20 |
| Germanium | 5 |

These ingredients are uniformly admixed to obtain the composition of the present invention which is useful for treating stiffness of the shoulders and providing good sleep.

EXAMPLE 2

| Ingredient | % by weight |
| --- | --- |
| Ethylene vinyl acetate foaming binder | 53 |
| Acrylate copolymer stretch binder | 14 |
| Ethylene imine cross linking agent | 3 |
| Far infrared irradiating ceramic | 20 |
| Germanium | 10 |

These ingredients are uniformly admixed to obtain the composition of the present invention which is useful for treating severe stiffness of the shoulders and pain of the elbow.

EXAMPLE 3

| Ingredient | % by weight |
| --- | --- |
| Acrylonitrile copolymer foaming binder | 49 |
| Polyurethane stretch binder | 13 |
| Isocyanate cross linking agent | 3 |
| Far infrared irradiating ceramic | 25 |
| Germanium | 10 |

These ingredients are uniformly admixed to obtain the composition of the present invention which is useful for treating pain of the knee, lumbago and menorrhalgia.

EXAMPLE 4

| Ingredient | % by weight |
| --- | --- |
| Acrylate copolymer stretch binder | 62 |
| Isocyanate cross linking agent | 3 |
| Far infrared irradiating ceramic | 25 |
| Germanium | 10 |

These ingredients are uniformly admixed to obtain the composition of the present invention which is useful for treating pain of the knee, lumbago and menorrhalgia.

EXAMPLE 5

| Ingredient | % by weight |
| --- | --- |
| Polyurethane binder | 62 |
| Urethane cross linking agent | 3 |
| Far infrared irradiating ceramic | 20 |
| Germanium | 15 |

These ingredients are uniformly admixed to obtain the composition of the present invention which is useful for treating severe lumbago and menorrhalgia.

EXAMPLE 6

| Ingredient | % by weight |
| --- | --- |
| Ethylene vinyl acetate foaming binder | 20 |
| Acrylate copolymer stretch binder | 42 |
| Urethane cross linking agent | 3 |
| Far infrared irradiating ceramic | 20 |
| Germanium | 15 |

These ingredients are uniformly admixed to obtain the composition of the present invention which is useful for treating severe lumbago and menorrhalgia.

EXAMPLE 7

| Acrylate copolymer stretch binder | 67 |
| --- | --- |
| Ethylene imine cross linking agent | 3 |
| Far infrared irradiating ceramic | 20 |
| Germanium | 10 |

These ingredients are uniformly admixed to obtain the composition of the present invention which is useful for pressing against the shoulder and the sole of the foot.

The following clinical tests illustrate the therapeutic effect of the sheet material for skin contact medical treatment of the present invention.

TEST 1

The patient was a 43 year-old man suffering from pain and stiffness of the shoulders and neck for a long period of time. The cloths shown in FIG. 1 having 110 therapeutically effective parts (60 mm × 110 mm) were applied to both sides of his shoulders and neck on 4 to 5 days after remarkable manifestation of pain and stiffness. According to him, pain and stiffness were mitigated very well on the next day and he felt relieved.

TEST 2

The patient was a 53 year-old woman sometimes suffering from pain of both brachia. The cloth as described in Test 1 was sewed directly on a supporter and it was put on her diseased part. From the next morning, no pain was felt.

When the supporter was taken off, she felt pain again after several days. Then, she put on the supporter for 2 days. As the result, according to her, no pain was felt and the conditions were almost healed.

TEST 3

The patient was a 48 year-old man suffering from pain of the left ankle for several months. He felt severe pain, particularly, when he went up or down stairs. When a supporter for a leg was described in Test 2 was put on his leg for 2 days, it eased pain of the ankle and he could go up or down the stairs without any difficulty.

TEST 4

The patient was a 87 year-old woman suffering from stiffness of the shoulders and neck and pain of the hands, arms, legs and waist. Various treatment such as physiotherapy, chiropractic techniques, massage and the like were less effective and her conditions were considerably serious. When the cloths of Test 1 were applied to her diseased parts for 3 days, it eased pain and stiffness and she felt relieved. According to her, the cloth was more effective in comparision with the above various treatments.

TEST 5

The patient was a 53 year-old women suffering from insomnia. When supporters of the cloths of Test 1 were applied to both ankles, she slept much better and deeper than usual and the sleeping time (6 hours) was longer than usual (4 hours). She did not have any dream.

TEST 6

The patient was a 72 year-old women suffering from insomnia and using a tranquilizer. When she wore a shirt of the cloth of Test 1 in bed, she slept well and half the amount of the tranquilizer was used.

What is claimed is:

1. A sheet material for skin contact medical treatment at least one part of which is a therapeutically effective part comprising germanium and ceramic which irradiates far infrared rays by heating, said germanium and ceramic being provided within a distance from 0 to 3 cm of each other in said therapeutically effective part.

2. A composition of therapeutically effective materials for skin contact medical treatment which comprises germanium powder and ceramic powder which irradiates far infrared rays by heating.

3. A composition according to claim 2, wherein the weight ratio of germanium as inorganic pure germanium: ceramic is 3 to 40:97 to 60.

4. A sheet material for skin contact medical treatment at least one part of which is a therapeutically effective part comprising germanium and ceramic which irradiates far infrared rays by heating, said germanium and ceramic being provided within a distance of 0 to 3 cm of each other in said therapeutically effective part, and wherein the therapeutically effective part is a cloth composed of yarns coated with a composition of therapeutically effective materials comprising germanium powder and ceramic powder which irradiates far infrared rays by heating.

5. A sheet material according to claim 4, wherein the composition contains germanium and ceramic in a weight ratio of germaium as inorganic pure germanium : ceramic of 3 to 40:97 to 60.

6. A sheet material for skin contact medical treatment at least one part of which is a therapeutically effective part comprising germanium and ceramic which irradiates far infrared rays by heating, said germanium and ceramic being provided within a distance of 0 to 3 cm of each other in said therapeutically effective part, and wherein the therapeutically effective part is a coated film of a composition of therapeutically effective material comprising germanium powder and ceramic powder which irradiates far infrared rays by heating.

7. A sheet material according to claim 6, wherein the composition contains germanium and ceramic in a weight ratio of germanium as inorganic pure germanium:ceramic of 3 to 40:97 to 60.

8. A sheet material for skin contact medical treatment at least one part of which is a therapeutically effective part comprising germanium and ceramic which irradiates far infrared rays by heating, said germanium and ceramic being provided within a distance of 0 to 3 cm of each other in said therapeutically effective part, and wherein one surface of the therapeutically effective part which is not brought into contact with the skin is covered with a metallic film.

9. A sheet material for skin contact medical treatment at least one part of which is a therapeutically effective part comprising germanium and ceramic which irradiates far infrared rays by heating, said germanium and ceramic being provided within a distance of 0 to 3 cm of each other in said therapeutically effective part, and wherein the therapeutically effective part is a laminate of a germanium thin film and a ceramic thin film.

* * * * *

UNITED STATES PATENT AND TRADEMARK OFFICE
CERTIFICATE OF CORRECTION

PATENT NO. : 4,976,706

DATED : December 11, 1990

INVENTOR(S) : Osami AKI et al.

It is certified that error appears in the above-identified patent and that said Letters Patent is hereby corrected as shown below:

Below the patent number at the top of the title page, in item [45], delete the asterisk (*) before the date "Dec. 11, 1990".

On the title page, left column, delete "[*] Notice: The portion of the term of this patent subsequent to Dec. 12, 2007 has been disclaimed.".

Signed and Sealed this

Ninth Day of June, 1992

Attest:

DOUGLAS B. COMER

*Attesting Officer*     Acting Commissioner of Patents and Trademarks